(12) United States Patent
Jayaraman

(10) Patent No.: US 6,224,625 B1
(45) Date of Patent: May 1, 2001

(54) LOW PROFILE HIGHLY EXPANDABLE STENT

(75) Inventor: Swaminathan Jayaraman, Dallas, TX (US)

(73) Assignee: Iowa-India Investments Company Limited, Douglas (GB)

(*) Notice: Subject to any disclaimer, the term of this patent is extended or adjusted under 35 U.S.C. 154(b) by 0 days.

(21) Appl. No.: 08/958,104

(22) Filed: Oct. 27, 1997

(51) Int. Cl.⁷ ...................................................... A61F 2/06
(52) U.S. Cl. .......................................... 623/1.15; 623/1.13
(58) Field of Search .................................. 623/1, 12, 1.1, 623/1.11, 1.12, 1.13, 1.15, 1.16, 1.17, 1.18, 1.19, 1.21, 1.22; 606/194, 198

(56) References Cited

U.S. PATENT DOCUMENTS

| | | |
|---|---|---|
| 4,441,215 | 4/1984 | Kaster . |
| 4,728,328 * | 3/1988 | Hughes et al. ........................ 623/12 |
| 5,383,892 * | 1/1995 | Cardon et al. ....................... 606/198 |
| 5,556,413 * | 9/1996 | Lam ....................................... 606/198 |
| 5,562,725 | 10/1996 | Schmitt et al. . |
| 5,562,727 | 10/1996 | Turk et al. . |
| 5,562,728 * | 10/1996 | Lazarus et al. ........................... 623/1 |
| 5,665,117 * | 9/1997 | Rhodes ..................................... 623/1 |
| 5,667,523 * | 9/1997 | Byron et al. .......................... 606/198 |
| 5,713,917 * | 2/1998 | Leonhardt et al. ................... 606/194 |
| 5,733,325 * | 3/1998 | Robinson et al. ........................ 623/1 |
| 5,843,162 * | 12/1998 | Inoue ....................................... 623/1 |
| 5,843,175 * | 12/1998 | Frantzen .................................. 623/1 |
| 5,868,783 * | 2/1999 | Tower ................................... 606/198 |
| 5,871,536 * | 2/1999 | Lazarus ................................... 623/1 |
| 5,964,798 * | 10/1999 | Imran ...................................... 623/1 |

* cited by examiner

Primary Examiner—David H. Willse
Assistant Examiner—Alvin Stewart
(74) Attorney, Agent, or Firm—Larson & Larson, P.A.; James E. Larson

(57) ABSTRACT

A stent is disclosed in several embodiments including the use of a material known as NITINOL forming the ends of the stent as well as support structure connecting the ends. A fabric is interconnected with the NITINOL structure to form the stent. The NITINOL material ends have slits parallel with the direction of elongation of the stent allowing radial expansion of the ends. The pieces interconnecting the ends have a serpentine shape allowing longitudinal expansion of the stent. The NITINOL material structure may be located within the fabric portion or outside the fabric portion. The connecting pieces may be separate structures attached to the fabric. Alternatively, the end pieces may be separate structures attached to the fabric without the connecting pieces.

13 Claims, 2 Drawing Sheets

LOW PROFILE HIGHLY EXPANDABLE STENT

BACKGROUND OF THE INVENTION

1. Field of the Invention

The present invention relates to a stent. More particularly, it relates a low profile highly expandable stent.

2. Description of the Prior Art

Stents for use in transluminal implantation are known in the prior art. Most are known to be balloon expandable, self-expandable, or thermally expandable. But, the degree of expansion in these prior art stents are determined by the diameter of the balloon used to cause the expansion or of the diameter of an artery when using self-expanding or thermally expanding means. An improved stent is needed in which the degree of expansion in the stent is not constrained by diameter of the balloon or of the artery.

Some prior art stents are known to comprise rigid and flexible portions. U.S. Pat. No. 5,383,892 ('892) to Cardon et al. disclose a stent employing at least two cylindrical rigid parts and at least one flexible part where the flexible part is welded to the rigid parts. Such a stent could be considered a combination stent utilizing a graft or other material. The invention of '892 is adapted such that the rigid parts expand radially in a plastic manner and flexible parts expand radially in an elastic manner. Unfortunately, the degree of expansion of the '892 stent is determined by the balloon used to expand the stent or the elastic nature of the metal used on the rigid parts. Such prior art stents are very limited in their degree of expansion and are not capable of the high degree of expansion seen in the stent of the present invention. In such a stent, it is necessary to form the stent having a very large profile, so that the higher degree of expansion can be achieved. However, large profile stents are not desirable due to the fact that they can not be used in minimally evasive surgical procedures. Requiring large incisions in the body and the artery only acts to complicate the surgical procedure and adds additional risk to the patient.

An improved stent is needed that utilizes combination stent-graft techniques and is capable of a high degree of expansion, yet retain a low profile so that surgeons can perform minimally evasive surgical procedures and use such novel stent in a wide range of artery diameters. Such improved stent can be manufactured in one size, yet be used universally.

SUMMARY OF THE INVENTION

The present invention relates to a low profile highly expandable stent. The present invention includes the following interrelated objects, aspects and features:

(1) In a first aspect, the present invention contemplates a stent having a low profile and with structure permitting expansion multiple times its original diameter. For example, the stent may expand from its initial diameter of approximately 1.5 millimeters to up to 12 millimeters.

(2) In a first embodiment of the present invention, a sheet of a material known as NITINOL is cut to form two end pieces having longitudinal slits and interconnected with serpentine connecting pieces. The longitudinal slits in the end pieces permit radial expansion of the stent while the serpentine nature of the connecting pieces allows longitudinal expansion. When the sheet has been appropriately cut into the end pieces with their connecting pieces, the end pieces are rolled into cylindrical tubes with their ends interconnected to form a tubular stent structure. A piece of tubular, preferably, knitted, fabric is attached to the NITINOL material structure to form a finished stent. In one embodiment, the fabric is mounted within the NITINOL material. In another embodiment, the fabric is mounted outside the NITINOL material.

(3) In a further embodiment, only the NITINOL material end pieces are provided with the fabric material interconnecting them. In another embodiment, the fabric material is provided and only the NITINOL material connecting pieces are mounted in circumferentially spaced relation about the circumference of the fabric material.

(4) In an alternate embodiment, a tubular piece of material is substituted for the sheet of material. The end piece slits are formed by making small cuts in the material; in other words, material is not removed. The serpentine connecting pieces are then formed by removing material from the tubular piece of material through the use of a laser cutting machine, a chemical etching machine, an electron beam cutting machine or any other suitable device. The tubular fabric may then be mounted on the inside or outside of the serpentine connecting pieces.

(5) In any of the embodiments of the present invention, the stent is conveyed to the location of application in a collapsed configuration and is expanded in place in any suitable manner such as through inflation of a balloon catheter therewithin or by use of thermal expansion.

Accordingly, it is a first object of the present invention to provide a low profile highly expandable stent.

It is a further object of the present invention to provide such a stent including end pieces and/or connecting pieces made of a NITINOL material.

It is a further object of the present invention to provide such a stent including a tubular piece of fabric mounted either within or surrounding the NITINOL material structure.

It is a still further object of the present invention to provide such a stent with longitudinal slits in the end pieces thereof and with the connecting pieces made in a serpentine configuration.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
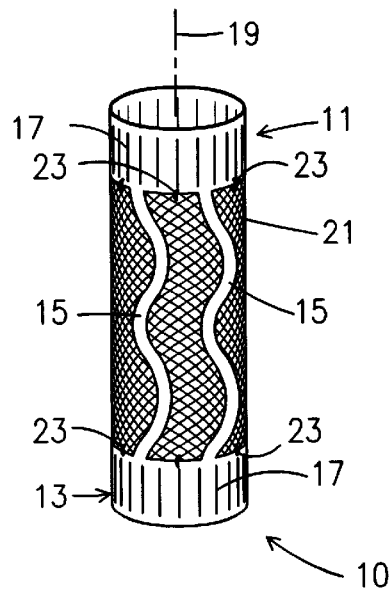
FIG. 1 shows a side perspective view of a first embodiment of the present invention.

With reference, first, to FIG. 1, a first embodiment of the present invention is generally designated by the reference numeral 10 and is seen to include a framework consisting of end pieces 11 and 13 interconnected with connecting pieces 15. The end pieces 11 and 13 have spaced slits 17 that allow radial expansion. In the preferred embodiment, slits 17 are formed by cutting the material that form end pieces 11 and 13. The connecting pieces 15 are serpentine in configuration allowing longitudinal expansion along the axis 19 of elongation of the stent 10.

Figure 2:
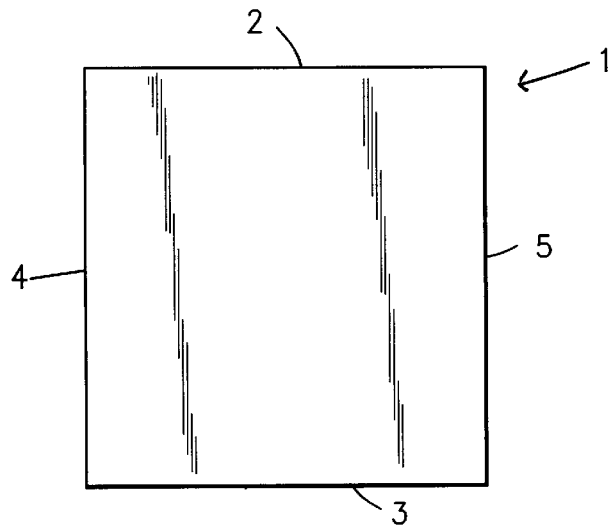
FIG. 2 shows a generally rectangular sheet of NITINOL material used in forming a portion of the structure of the stent of FIG. 1.
Figure 3:
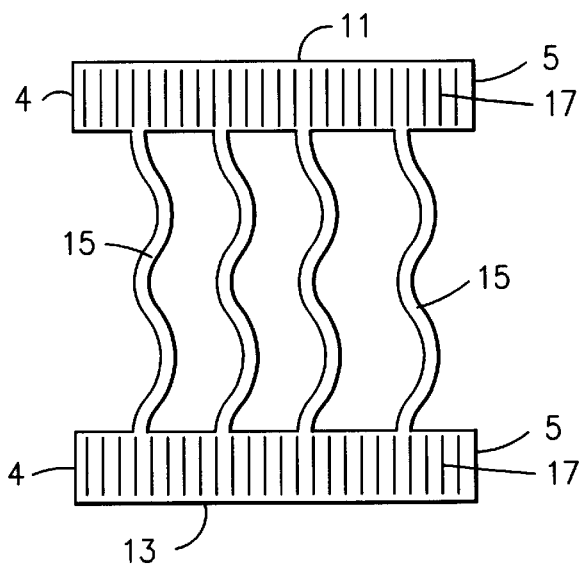
FIG. 3 shows the sheet of NITINOL material depicted in FIG. 2 but with pieces thereof cut away and slits formed therein to form the NITINOL structure of the stent.

FIG. 2 depicts a piece 1 of NITINOL material that is generally rectangular including ends 2, 3 and side edges 4 and 5. With reference to FIG. 3, it is seen that the sheet 1 of NITINOL material may be cut with any suitable cutting means to form the structure shown in FIG. 3. The structure shown in FIG. 3 includes the end pieces 11 and 13 as well as the connecting pieces 15 before the end pieces 11 and 13 have been rolled into the cylindrical shapes shown in FIG. 1. The side edges 4, 5 abut one another when the end pieces 11, 13 have been rolled into the cylindrical shape shown in FIG. 1. These edges 4, 5 are affixed to one another in any suitable manner such as by stitching, suturing, adhesive, ultrasonic welding, or any other method. Although the preferred embodiment employs NITINOL, it is understood that the invention contemplates use of other self-expanding and thermally expanding metals.

Figure 4:
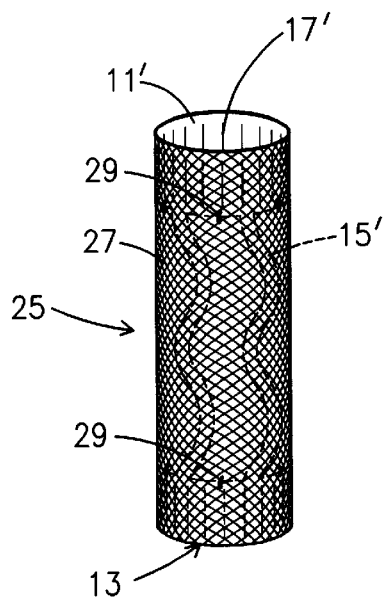
FIG. 4 shows a second embodiment of the present invention wherein the fabric portion thereof is outside the NITINOL material structure.

With reference back to FIG. 1, a cylindrical tube is designated by the reference numeral 21 and is seen to be inserted within the structure of the end pieces 11, 13 and the connecting pieces 15. In the preferred embodiment, a fabric tube is employed although in an alternate embodiment an extruded tube may be employed. Further, tube 21 may be made of synthetic or biologic material or a combination of both. If synthetic material is used for tube 21, it may be extruded, woven, or knitted. Tube 21 is attached to the structure of the end pieces 11, 13 and the connecting pieces 15 by any suitable means such as, for example, stitching 23. An alternative construction is seen with reference to FIG. 4 wherein like structures are designated using like primed reference numerals. Thus, the stent 25 depicted in FIG. 4 includes end pieces 11' and 13' interconnected by serpentine shaped connecting pieces 15', with the end pieces 11', 13' including longitudinal slits 17'. A fabric tube 27 is formed of a size such that it fits over the outside of the end pieces 11' and 13' as well as the connecting pieces 15'. The tube 27 may be affixed to the end pieces 11', 13' and the connecting pieces by any suitable means such as, for example, the stitching 29. Again, in an alternate embodiment, an extruded tube is used for tube 27.

Figure 5:
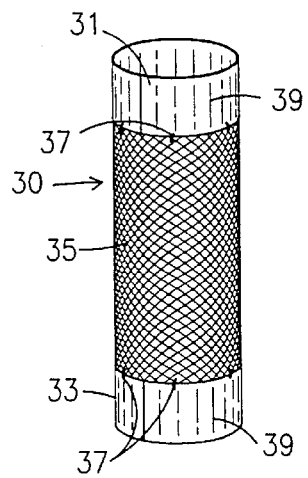
FIG. 5 shows a third embodiment of the present invention wherein only the end pieces of NITINOL material are employed and the fabric portion is interconnected therebetween.
Figure 6:
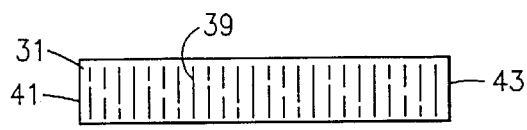
FIG. 6 shows one of the NITINOL material end pieces of the embodiment of FIG. 5 before it is rolled into a cylindrical shape.

With reference, now, to FIGS. 5 and 6, a third embodiment of the present invention is generally designated by the reference numeral 30 and is seen to include end pieces 31 and 33 as well as a fabric tube 35 interconnecting the end pieces 31 and 33 and affixed thereto through any suitable means such as, for example, the stitching 37. End pieces 31 and 33 include longitudinal slits 39 allowing radial expansion of end pieces 31 and 33. End pieces 31 and 33 may have the same structure as the end pieces 11 and 13 and 11' and 13' described above. FIG. 6 shows the end piece 31 after it has been cut from a piece of NITINOL material such as the sheet 1 illustrated in FIG. 2 and after the slits 39 have been cut therein. The piece 31 has side edges 41 and 43 that abut one another when the piece 31 is rolled into the cylindrical shape shown in FIG. 5. These edges 41 and 43 may be affixed to one another by any suitable means such as adhesive, stitching or ultrasonic welding. In an alternate embodiment, tubular pieces of material are used for end pieces 31 and 33. Longitudinal slits 39 are cut into the tubular end pieces using any suitable means. As in the first and second embodiments, the tube 35 may be an extruded tube.

Figure 8:
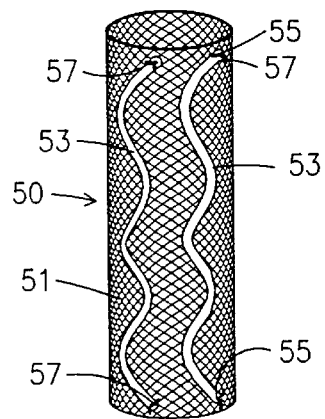
FIG. 8 shows a fourth embodiment of the present invention utilizing connecting pieces such as depicted in FIG. 7 interconnected to a fabric tube.
Figure 7:
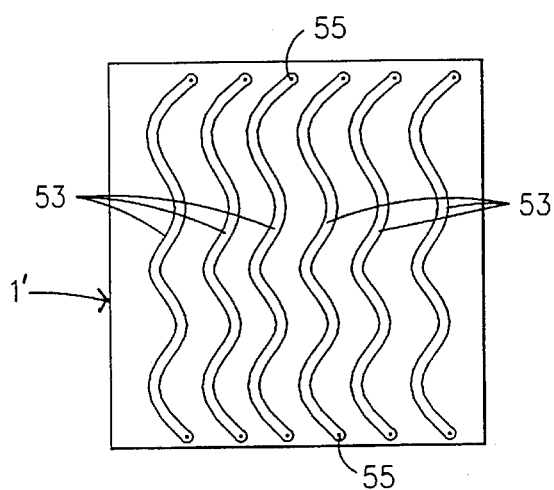
FIG. 7 shows a sheet of NITINOL material such as is shown in FIG. 2 with the outline of cuts to be made to form connecting pieces shown thereon.

With reference to FIGS. 7 and 8, a fourth embodiment of the present invention is described. As shown in FIG. 8, the fourth embodiment of the present invention is generally designated by the reference numeral 50 and includes a fabric tube 51 to which are affixed connecting pieces 53, each of which has a serpentine shape and is circumferentially spaced from adjacent connecting pieces 53. Each end of each connecting piece 53 has a hole 55 therethrough allowing interconnection of the connecting pieces 53 to the fabric tube 51 by suitable means such as stitching or sutures 57.

With reference to FIG. 7, a piece 1' of NITINOL material is seen to have the connecting pieces 53 cut therefrom including the holes 55 formed at each end thereof.

If desired, the connecting pieces 53 may be suitably affixed inside the fabric tube 51.

In the stent of the present invention, it is possible to have infinite expansion rates based on the design that is cut on the surface of the NITINOL material. In the preferred embodiment, the stent in its collapsed state may have a diameter in the range of 1.5 millimeters. Such stent may be expandable up to eight times to a diameter of, for example, 12 millimeters.

It is also contemplated that the stent of the present invention along with the longitudinal sections can be additionally expanded with a delivery mechanism, such as a balloon catheter. Such employment, if needed, could ensure final expansion of the stent to the resultant diameter desired.

As such, an invention has been disclosed in terms of preferred embodiments thereof which fulfill each and every one of the objects of the invention as set forth hereinabove and provide a new and useful low profile highly expandable stent of great novelty and utility.

Of course, various changes, modifications and alterations may be contemplated by those skilled in the art without departing from the intended spirit and scope thereof.

As such, it is intended that the present invention only be limited by the terms of the appended claims.

What is claimed is:

1. A low profile, highly expandable stent, comprising:
   a) a framework having two spaced non-cuffed, generally cylindrical monolayer end pieces;
   b) a tubular member interconnecting solely with said end pieces;
   c) the end pieces having a plurality of circumferentially spaced longitudinal slits;
   d) the end pieces connected to the tubular member with stitching to form a one piece integral unit;
   e) a plurality of spaced apart longitudinal members interconnecting the end pieces so that from a fully compressed state, the stent will expand both radially and longitudinally from a diameter and a length of the compressed state, when released in a lumen of a patient; and
   f) the stitching disposed at points along the end pieces in between each of the plurality of spaced apart longitudinal members.

2. The stent of claim 1, wherein each of said longitudinal members has a serpentine shape.

3. The stent of claim 1, wherein said longitudinal members are circumferentially spaced about said end pieces.

4. The stent of claim 1, wherein said tubular member is within said longitudinal members.

5. The stent of claim 1, wherein said tubular member surrounds said longitudinal members.

6. The stent of claim 5, wherein said tubular member surrounds said end pieces.

7. The stent of claim 1, wherein said end pieces are made of a nickel-titanium alloy.

8. The stent of claim 2, wherein said end pieces and the longitudinal members are made of a nickel-titanium alloy.

9. The stent of claim 1, wherein said tubular member is a fabric tube.

10. A low profile, highly expandable stent, comprising:

a) a fabric tubular member;

b) a plurality of circumferentially spaced apart connecting members having first and second ends, the connecting members unconnected but juxtaposed to the tubular member to promote longitudinal expansion of the stent;

c) the fabric tubular member interconnecting solely by stitching with a non-cuffed end piece at a first and second end, the stitching disposed at points along the end pieces in between each of the plurality of circumferentially spaced apart connecting members;

d) the connecting members integral with an end piece at the first and second end of each connecting member; and e) a plurality of circumferentially spaced longitudinal slits formed in each end piece whereby the stent expands radially from its initial diameter of about 1.5 mm to up to 12 mm in a patient's lumen.

11. The stent of claim 10, wherein each of said connecting members is serpentine in shape.

12. The stent of claim 10, wherein said connecting members are attached outside said tubular member.

13. The stent of claim 10, wherein said connecting members are made of a nickel-titanium alloy.

* * * * *